(12) United States Patent
Spitz et al.

(10) Patent No.: US 8,708,196 B2
(45) Date of Patent: Apr. 29, 2014

(54) AMPOULE PROTECTOR AND METHOD OF CONSTRUCTION THEREOF

(75) Inventors: Joseph J. Spitz, Baraboo, WI (US); Robert C. Asam, Baraboo, WI (US)

(73) Assignee: Teel Plastics, Inc., Baraboo, WI (US)

( * ) Notice: Subject to any disclaimer, the term of this patent is extended or adjusted under 35 U.S.C. 154(b) by 67 days.

(21) Appl. No.: 13/328,266

(22) Filed: Dec. 16, 2011

(65) Prior Publication Data
US 2012/0157940 A1   Jun. 21, 2012

Related U.S. Application Data

(60) Provisional application No. 61/423,738, filed on Dec. 16, 2010.

(51) Int. Cl.
*A47G 19/00* (2006.01)
*A61M 35/00* (2006.01)

(52) U.S. Cl.
USPC ........................................ 222/142.5; 222/129

(58) Field of Classification Search
USPC .......... 604/289, 290, 403; 222/129; 215/12.2; 401/132; 128/203.21; 206/530; 225/93
See application file for complete search history.

(56) References Cited

U.S. PATENT DOCUMENTS

| | | | |
|---|---|---|---|
| 2,546,848 A | 3/1951 | Rogers | |
| 3,757,782 A | 9/1973 | Aiken | |
| 4,304,869 A | 12/1981 | Dyke | |
| 4,779,763 A | 10/1988 | Klawitter | |
| 4,967,539 A | 11/1990 | Hansen | |
| 5,133,458 A | 7/1992 | Miller | |
| 5,256,537 A | 10/1993 | Phillips et al. | |
| 5,288,159 A | 2/1994 | Wirt | |
| 5,320,257 A | 6/1994 | Snedden | |
| 5,435,660 A | 7/1995 | Wirt | |
| 5,658,084 A | 8/1997 | Wirt | |
| 6,039,488 A | 3/2000 | Krawczyk et al. | |
| 6,340,097 B1 | 1/2002 | D'Alessio et al. | |
| 6,478,191 B1 | 11/2002 | D'Alessio et al. | |
| 6,846,459 B2 | 1/2005 | Snedden | |
| 7,261,701 B2 | 8/2007 | Davis et al. | |
| 7,308,782 B2 | 12/2007 | Hansen | |
| 7,374,802 B2 | 5/2008 | Zihlmann | |
| 2003/0080151 A1 | 5/2003 | D'Alessio | |
| 2004/0096666 A1* | 5/2004 | Knox et al. | 428/412 |
| 2005/0072442 A1 | 4/2005 | Licari et al. | |
| 2005/0111900 A1 | 5/2005 | Fazzolari | |
| 2007/0262045 A1 | 11/2007 | Hansen | |

\* cited by examiner

*Primary Examiner* — Melanie Hand
(74) *Attorney, Agent, or Firm* — Boyle Fredrickson, S.C.

(57) ABSTRACT

A fluid delivery device includes a compressible sleeve configured to hold a fluid-holding container such as an ampoule or capsule. The sleeve is compressible so as to be able to shatter the container under user-applied force to release the contents of the container for application to a desired location. The sleeve is constructed from at least two independent and separate walls. The independence of the walls improves the resistance of the sleeve to accidental puncturing by the frangible container while not significantly impacting the force required to shatter the container.

20 Claims, 3 Drawing Sheets

AMPOULE PROTECTOR AND METHOD OF CONSTRUCTION THEREOF

CROSS-REFERENCE TO RELATED APPLICATIONS

This application claims priority to U.S. Provisional Patent Application No. 61/423,738 filed on Dec. 16, 2010 and entitled Ampoule Protector and Method of Construction Thereof, the entirety of which is hereby incorporated by explicit reference thereto.

BACKGROUND OF THE INVENTION

This invention relates to fluid delivery devices, and more particularly, to fluid delivery devices including a holder such as sleeve for at least partially enclosing a fluid holding container such as an ampoule or capsule, wherein the fluid holding container is selectively breakable by user-applied pressure to the sleeve.

It is generally known to provide a liquid delivery device including a sleeve that is configured to receive a crushable container such as an ampoule or capsule. The container typically includes a liquid that is to be applied to a desired location through, for example, an optional applicator. Typically, such sleeves are constructed of a single tube or a single tube composed of multiple layers formed together via a standard coextrusion process. In a coextruded construction, layers of the tube of the sleeve are typically coupled to one another by chemical adhesion or by a tie layer or the like. In some cases a rubber urethane tie layer is used as a functional layer between layers. The container is securable within a cavity defined by the sleeve and is typically constructed from glass or a similarly breakable material. The user applies a force to the sleeve sufficient to shatter or otherwise crush the container contained within the sleeve so that the fluid held within the container is released into the sleeve and may then be selectively dispensed via the applicator or similar element. When used in the coextruded type sleeve, the rubber urethane layer is thought to blunt the penetration of the container material into the outer tube of the coextruded holder to prevent the material from contacting the user.

While assemblies of this kind are well known in the art, such assemblies suffer from a number of known disadvantages. For instance, such assemblies can result in an undesirable number of accidental punctures typically through repeated or overly aggressive pressing on the sleeve.

Other known types of fluid delivery devices have sought to remedy the deficiencies of known fluid delivery devices by providing sleeves having thicker walls or considerably thicker coextruded layers. Others have provided independent paperboard sleeves for the user that slides over the plastic sleeve to provide additional puncture protection. These have the disadvantage of requiring a secondary manufacturing step of producing a paper sleeve as well as the added assembly of it to the finished unit. However, these types of fluid delivery devices require an undesirable amount of additional crushing force to be applied by the user to the sleeve to break the enclosed container for dispensing the fluid. Thus, it can be difficult for a user of such devices to break the container for selective dispensing of the fluid contained therein. In addition, these types of fluid delivery devices can still result in an undesirable amount of accidental punctures.

Accordingly, a liquid delivery assembly that alleviates or eliminates one or more of the foregoing disadvantages is desired.

SUMMARY OF THE INVENTION

The present invention is generally directed to a fluid delivery device. The fluid delivery device includes a sleeve defining a cavity for receiving a frangible fluid container such as an ampoule or capsule. The fluid delivery device may include a delivery element such as an applicator for applying the fluid, which is coupled to the sleeve for selective application of the fluid.

The sleeve includes at least two separate and independent tubes or walls of material. The material of the tubes or walls may be a plastic or other material having similar characteristics. The inner tube or wall of the sleeve may be formed by way of a standard extrusion process and then cooled. The outer tube or wall is applied over the inner tube or wall, but is not physically or chemically bonded with the inner tube or wall. Instead, the outer tube or wall intimately surrounds the inner tube or wall, which provides a sleeve having improved puncture resistance while still being relatively easily compressible so as to shatter or crush the container held within the sleeve.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF PREFERRED EMBODIMENTS

Figure 1:
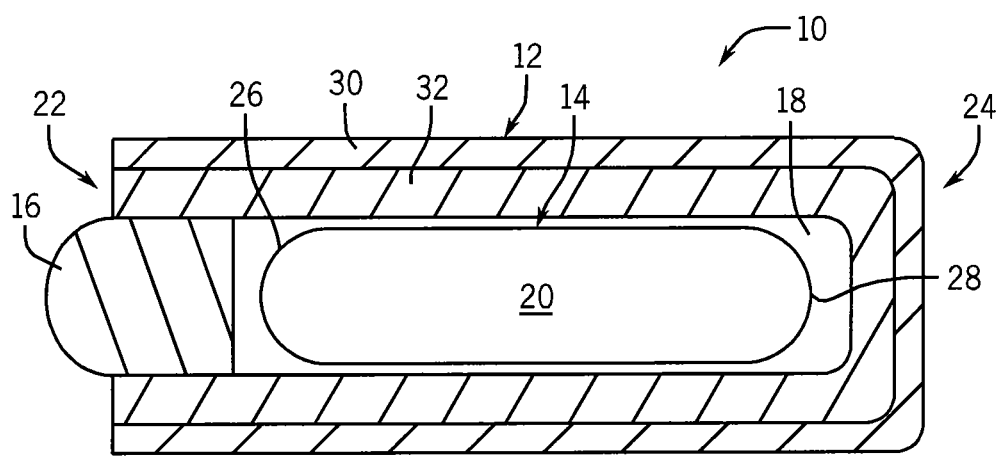
FIG. 1 is a longitudinal cross-sectional view of the fluid delivery device of an exemplary, first embodiment according to the present invention.

Referring now to the drawings and initially FIG. 1, a fluid delivery device 10 according to the invention includes a sleeve 12, a container 14 such as an ampoule or capsule (hereinafter "ampoule 14") that contains a fluid and that is at least partially secured within the sleeve 12, and an applicator 16 receivable within an end of the sleeve 12 and which may extend outwardly therefrom for selective application of the fluid to a desired location. The sleeve 12 may be generally hollow and include a cavity 18 for receiving the ampoule 14. As shown in FIG. 1, the ampoule 14 may be held such that its outer surfaces are spaced inwardly from the facing inner surface defined by the sleeve 12; however, it is to be understood that the ampoule 14 may be held within the sleeve 12 in close contact with the inner surface defined by the sleeve 12. The ampoule 14 may likewise be generally hollow and include a cavity 20 for holding the fluid. The sleeve 12 and the ampoule 14 may be generally tubular in shape having a generally circular cross-section or may have any other such shape as desired.

As will be discussed in additional detail, the sleeve 12 of the present invention is constructed from at least two independent and separate tubes or walls of material, shown at 30 and 32. For the sake of convenience, the tubes or walls 30, 32 will hereafter be referred to as walls 30, 32. The walls 32 may be formed of a material such as a plastic that is pliable or bendable while maintaining a desired amount of stiffness to enable the user to selectively shatter the ampoule 12 but to also provide the necessary structural integrity necessary to prevent accidental breaking and to prevent penetration by the shattered ampoule 14. By maintaining the at least two walls 30, 32 independent and separate from one another, the crushing force required to break the ampoule 14 is minimized while the resistance to penetration of the sleeve 12 is also improved as will be discussed in detail herein. The at least two walls 30, 32 may be constructed from the same or different materials.

The sleeve 12 may have a first end 22 and a second end 24 opposite the first end 22. As illustrated, the first end 22 includes an opening in which the applicator 16 may be received, and the second end 24 is closed, sealed, or otherwise configured to prevent the loss of fluid from the fluid delivery device 10 other than through the applicator 16 when the ampoule 16 is broken. The first end 22 may have a solvent or the like applied thereto for softening the area of the sleeve 12 around the opening to accommodate insertion of the applicator 16. The softening of the material enables the applicator 16 to be inserted under pressure and thereafter become "knit" or otherwise coupled with the sleeve 12 so as to keep it in place after evaporation of the applied solvent and the subsequent hardening of the area covered thereby. Alternatively, the applicator 16 may be integrally formed with the sleeve 12. Understandably, the sleeve 12 may include alternative constructions wherein both the first end 22 and the second end 24 are open or closed or in which the first end 22 is closed and the second end 24 is open.

The ampoule 14 may be made from glass or a similarly crushable material such that when the user applies a force to the sleeve 12, the ampoule 14 is broken and the fluid contained in the ampoule cavity 20 is released into the cavity 18 of the sleeve 12. The applicator 16 may be a pledget, nozzle, or the like. The fluid may then be directed toward the applicator 16 under gravity or by squeezing sleeve 20, such that it becomes saturated or otherwise inundated with the fluid for selective delivery thereof. As is generally understood, the applicator 16 may be configured so as to prevent the introduction of any of the shattered pieces of the ampoule 14 into the applicator 16 so as to prevent the accidental dispensing thereof.

The ampoule 14 may include a pair of opposing ampoule ends 26 and 28, which may be sealed by welding or a similar method. The sealed ampoule 14 protects the integrity of the fluid contained therein by preventing fluid loss and the ingress of gases, water vapor, or other fluids that may be deleterious to the shelf life of the fluid. Oftentimes, the fluid contained in the ampoule 14 is for use in medical applications such as, for example, the application of topical sterilants, antiseptics, ointments, skin adhesives and the like although, understandably, the fluid may be any fluid capable of use with the fluid delivery device 10 of the present invention.

Figure 2:
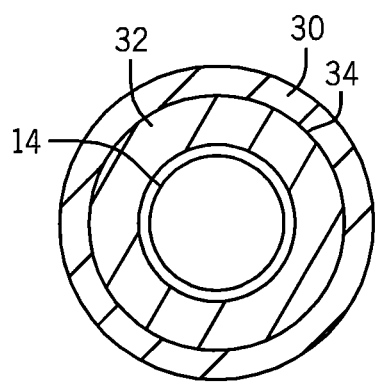
FIG. 2 is a transverse cross-sectional view of the fluid delivery device of FIG. 1*t*.
Figure 3:
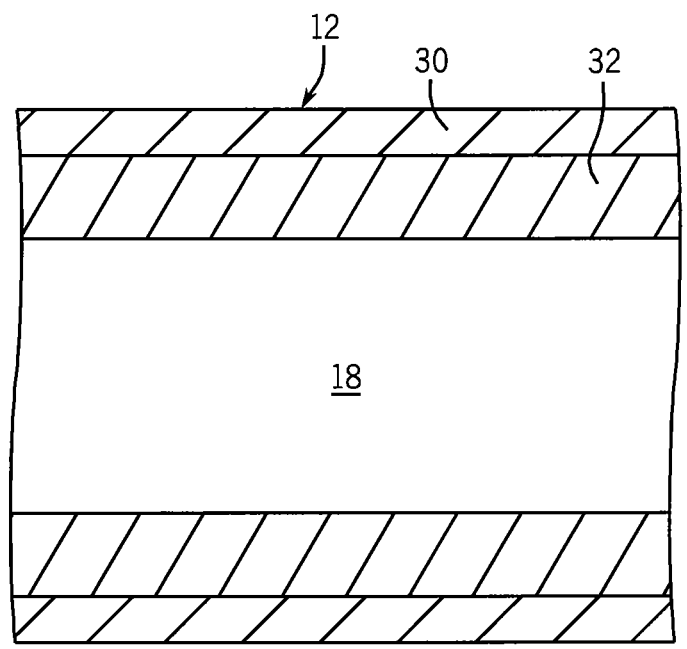
FIG. 3 is an enlarged view of a portion of the fluid delivery device of FIG. 1.
Figure 4:
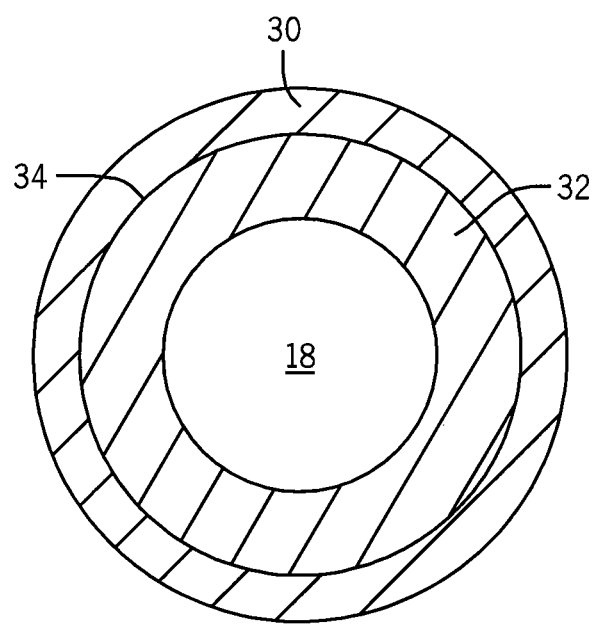
FIG. 4 is an enlarged view of a portion of the fluid delivery device as shown in FIG. 2.

With additional reference now to FIGS. 2-4, a first, exemplary, embodiment of the fluid delivery device 10 is illustrated in which the sleeve 12 includes the first or outer wall 30 and the second or inner wall 32. In the present embodiment, the outer wall 30 and the inner wall 32 each have a single-layer construction. The outer wall 30 and inner wall 32 may be constructed from a twin-tube sleeve material formed through a tandem or sequential process. During the process, the inner wall 32 is formed with a conventional tubing extrusion process and cooled. The inner wall 32 may then be advanced to a second extrusion location where it is surrounded by the outer wall 30 around its entire circumference. Understandably, in at least one construction of the present invention, the sleeve 12 may be configured such that the outer wall 30 is provided around a majority or only a portion of the circumference of the inner wall 32. For instance, the outer wall 30 may be applied about a portion of the inner wall 32 where the user is to compress the sleeve 12 for breaking the ampoule 14. The outer wall 30 also may surround the inner wall 32 a full 360 degrees but have varying thickness depending on the position around the inner wall 32.

The outer wall 30 and inner wall 32 may be constructed from the same or different material. The resulting sleeve 12 is constructed of two completely separate and independent walls that are closely formed with one another but which are not physically or chemically adhered to one another. With reference now to FIGS. 2-4, there may be a small peripheral space 34 between the outer wall 30 and the inner wall 32. The space 34 is exemplary only and is provided to illustrate the separate nature of the outer wall 30 and the inner wall 32. The spacing between the outer wall 30 and the inner wall 32 may be practically imperceptible, or the outer wall 30 and inner wall 32 may be physically in contact with one another but without being otherwise physically or chemically secured together.

By forming the sleeve 12 in this manner, the puncture resistance of the sleeve 12 is greatly improved as compared to layers that are physically, chemically or otherwise adhered to one another. In particular, each of the walls 30, 32 requires initiation of a separate tear propagation in order for the glass or similar material of the ampoule 14 to penetrate each of the respective walls 30, 32. By separating the walls, the direction of the ampoule 14 breaking is diffused. Further, the amount of crushing force necessary to shatter the ampoule 14 is reduced compared to equivalent materials in traditional constructions. This is because the force to bend or buckle the sleeve is determined by the moment of inertia of the wall thickness, which is a function of the position of each mass element from the center of the respective tube. Thus, the required crush force is reduced as the resultant moments are a summation of the moments of the two thinner masses. In this manner, the calculated crush strength or stiffness of the structure is lower while improving the puncture resistance of the fluid delivery device 10 due to the need to propagate a tear initiation for each wall. This enables the overall material thickness of the sleeve to be increased if desired for additional improvements in puncture resistance with marginal increases in the crush force required to break the inner ampoule.

The outer wall 30 and the inner wall 32 may be constructed from any number of materials including styrene butadiene copolymers, cellulose acetate butyrate (CAB), cellulose acetate proprionate (CAP), polycarbonate, copolyester, polyethylene tetrephtalate glycol (PETG), acrylonitrile-butadiene-styrene (ABS), polycarbonate (PC), cyclic olefin copolymers, polyamides, and the like. The walls 30, 32 of the sleeve 12 may be constructed from any number of alternative materials such as plastics and the like that are capable of deforming to allow the shattering of the enclosed ampoule 14 but which are also capable of preventing the penetration of the broken ampoule 14 through the walls 30, 32. Any number of alternative materials may be used for constructing the sleeve 12 so long as the material is compatible with the fluid to be dispensed, capable of relatively easily deforming under user-applied pressure, does not have a propensity to crack when flexed, and has a relatively high resistance to puncture.

The walls 30, 32 may be clear so that the user may visually examine the contents of the ampoule 14. Alternatively, one or more of the walls 30, 32 may be opaque. In the case of an opaque construction, at least one of the walls 30, 32 may include a filler or foam that is added during the extrusion or other process. Further, a coating may be applied and dried on the surface of the inner wall 32 that may become wetted and visible, similar to a dye, if the inner wall 32 becomes compromised. In this way, a user may be made aware of a potential contamination or degradation of the contents of the ampoule 14.

Still referring to FIGS. 2-4, as noted previously, the walls 30, 32 may be constructed from the same, similar, or different materials. Moreover, the walls 30, 32 may be constructed from the same material but have differing plasticizer concentrations. For example, one of the walls 30, 32 may include a relatively low amount of plasticizer, e.g. on the order of 5% plasticizer, while the other includes a higher amount of plasticizer, e.g. on the order of 13% plasticizer. The differential in plasticizer concentration serves to further optimize the crush force required and puncture resistance properties of the sleeve 12. As is generally understood in the art, the wall having the lower amount of plasticizer will be stiffer as compared to the wall having a higher amount. Thus, the wall with the lower amount of plasticizer requires greater crushing force to deform but has improved puncture resistance compared to the wall with the higher amount. Understandably, various plasticizer concentrations and combinations may be used and are contemplated to be within the scope of the present invention. For instance, the walls 30, 32 may have identical, more similar, or more disparate concentrations of plasticizer as may be desired.

Rather than providing one of the walls 30, 32 with differing amounts of plasticizer, an alternative method of altering the relative properties of the walls 30, 32 may be employed. For instance, in addition to or in the alternative, one of the walls 30, 32 may have an increased thickness relative to the other wall 30, 32.

In one construction of the sleeve 12, the walls 30, 32 may be incorporated into a single extrusion die head. The melted plastic or other material forming the wall 30 may be configured to exit the die head first, and once the material is cooled, the die head may be configured to deliver the material of the second wall 32. The die head may include different die tips configured to keep the dies separate from one another to thereby reduce the cost of producing the sleeve as compared to using two or more die heads.

In another construction, materials that are otherwise adhesively incompatible may be inserted between the walls 30, 32 to create three separate independent layers. For instance, two CAB layers may be extruded with a layer of polypropylene (PP) between them from a single die head using three separate extruders. The lack of chemical adhesion between the CAB and PP layers may cause the walls 30, 32 to delaminate during flexing. In yet another construction, the walls 30, 32 may be configured to separate from one another during cooling as a result of having differing thermal expansion coefficients or due to crystallization occurring in the PP layer.

Figure 5:
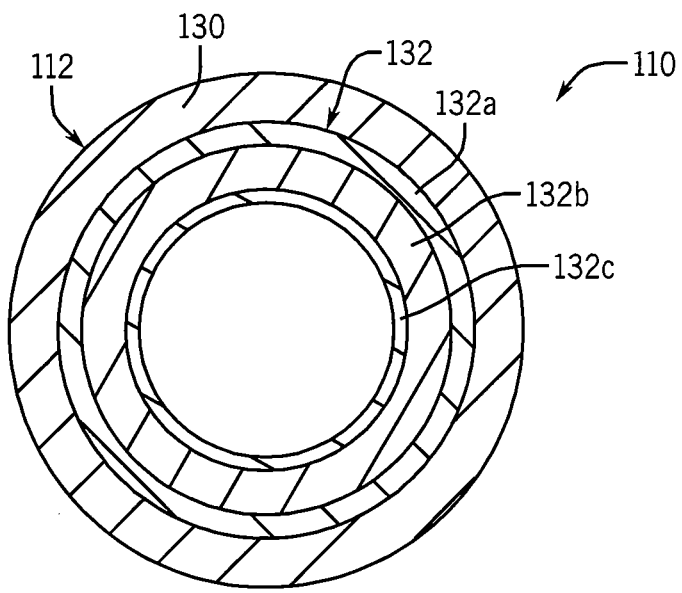
FIG. 5 is a transverse cross-sectional view of a fluid delivery device according to a second embodiment of the present invention.
Figure 6:
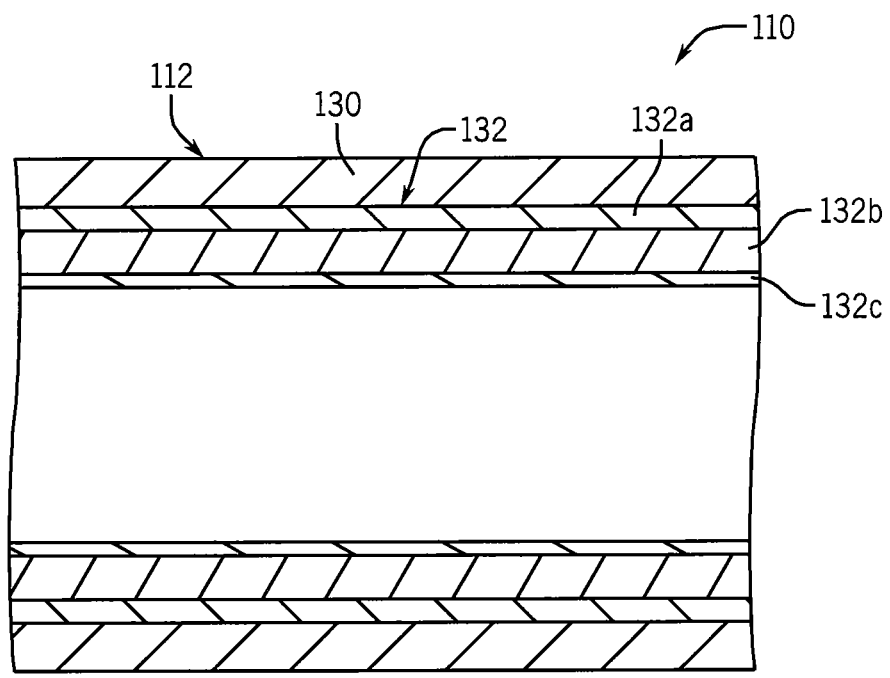
FIG. 6 is a partial longitudinal cross-sectional view of the fluid delivery device of FIG. 5.

Now referring to FIGS. 5 and 6, an alternative construction of a fluid delivery device of the present invention, shown at 110, is illustrated. The delivery device 110 of this embodiment may have a double wall construction, similar to that of delivery device 10, wherein one of the walls 130, 132 may include a number of coextruded sub-layers as will be discussed herein. As illustrated, the inner wall 132 of the sleeve 112 is constructed of an outermost inner sub-layer 132a, an intermediate inner sub-layer 132b, and an innermost inner sub-layer 132c. Understandably, the sleeve 112 may be constructed in an alternative manner such that the outer wall 130 includes the co-extruded sub-layers while the inner wall 132 has a single layer construction. Similarly, both the inner wall 132 and the outer wall 130 may be constructed from a number of sub-layers. The inner wall 132 is configured such that the sub-layers 132a-132c are physically coupled to one another in a traditional manner while the outer wall 130 and the inner wall 132 remain separate from one another. Understandably, the walls 130, 32 may be arranged in accordance with the walls 30, 32 and constructed in a similar manner as previously discussed.

In a first exemplary construction of the sleeve 112, the outer wall 130 may be constructed from a material such as CAB. The outer wall 130 may entirely surround the inner wall 132 in an independent and entirely separate manner as previously discussed. The outermost inner sub-layer 132a may be constructed from a CAB material, the intermediate inner sub-layer 132b may be constructed from a thermoplastic polyurethane (TPU) material, and the innermost inner sub-layer 132c may be constructed from a CAB material. Of course, any number of alternative materials may be used in constructing the sleeve 112 in accordance with the present embodiment.

Moreover, in another exemplary construction of the sleeve 112, the thicknesses of the walls 130, 132 may be configured to provide a desirable combination of stiffness to prevent puncturing and to maintain pliability to enable the user to easily crush the enclosed ampoule (not shown). For instance, in one construction, the outer wall 130 may be a 6 mil CAB layer, and the inner wall 132 may be 14 mil in total and include an outermost inner sub-layer 132a that is 6 mil CAB, an intermediate inner sub-layer 132b that is 2 mil TPU, and an innermost inner sub-layer 132c that is 6 mil CAB. Thus, the resulting sleeve 112 will have a thickness of about 20 mil. Such a construction will minimally increase the crushing force necessary to break the ampoule while greatly improving the resistance of the sleeve 12 to puncturing by the shards of the broken ampoule. Understandably, any of the walls 130, 132 may have differing thicknesses. For instance the outer wall 130 may be 8 or 10 mil thick or the like to provide a sleeve of about 22-24 mil thick. The resulting sleeve 112 will have an improved puncture resistance while still being relatively easy to compress so as to shatter the enclosed ampoule.

In practice, the inner wall such as 32 or 132 (referred to as 32 for convenience) is formed first by conventional means such as extrusion. Once the inner wall 32 is formed, it is cooled prior to having the outer wall 30 or 130 (referred to as 30 for convenience) applied thereto. In particular, as discussed previously, the outer wall 30 may be disposed about the inner wall 32 so as to surround it. However, the outer wall 30 is not bonded, physically or chemically, to the inner wall 32. In at least one embodiment of the present invention, the inner wall 32 may be cooled via a cooling tank or similar applicator so as to ensure that the inner wall 32 is sufficiently cooled by the time the outer wall 30 is applied. As the temperature of the die head applying the outer wall 30 may be sufficient to melt or elongate the inner wall 32, it is desired that the inner wall 32 be sufficiently cooled beforehand to reduce the likelihood of melting. For example, the inner wall 32 may be super-cooled as is generally understood to lower the temperature of the inner wall 32 to reduce the likelihood of melting. In such cases, it may be desirable to include a drying step to the process so as to remove any water or condensation that may have developed during the cooling of the inner tube 32. Moreover, it may be desired to maintain the inner wall 32 at a sufficient distance from the die head applying the outer wall 30 such that the die head does not physically contact the inner wall 32. In another construction of the sleeve 12, the die head applying the outer wall 30 may be fitted with a porcelain lead in insulator guide, or similar element, to minimize the contact between the die head and the inner wall 32. Also, it may be desirable to make the inner wall 32 thicker than the outer wall 30 so as to minimize any loss in thickness created by the application of the heat to the inner wall 32. For the reasons previously articulated, it is desirable to minimize the residence time that the inner wall 32 is in the hot coating zone of the die head applying the outer wall 30 thereto.

The present invention has been described in terms of representative embodiments, and it is recognized that equivalents, alternatives, and modifications, aside from those expressly stated, are possible and within the scope of the appending claims.

What is claimed is:

1. A fluid delivery device comprising:
a sleeve having a first end and a second end opposite the first end, the sleeve defining an opening at one of the first and second ends and a cavity between the first end and the second end, and wherein the sleeve is constructed from at least an outer wall and an inner wall that are arranged independently and separately from one another without a bond between the inner and outer walls, wherein the outer wall at least partially circumferentially surrounds the inner wall, and wherein the outer and inner walls are formed and arranged so as not to be separable from each other during use;
a breakable container located within the cavity that contains a fluid to be delivered, wherein the container is selectively breakable upon application of a transverse squeezing force to the sleeve to disperse the fluid to be delivered within the cavity and to enable the fluid to be dispensed through the opening;
wherein, when the transverse squeezing farce is applied to the sleeve, the transverse squeezing force is transferred first from the outer wall to the inner wall through an interface between the outer and inner walls, and then from the inner wall to the breakable container so as to break the container, and wherein the outer and inner walls and the interface between the outer and inner walls cooperate to inhibit penetration of the material of the breakable container through the sleeve after the breakable container has been broken by application of the transverse squeezing force.

2. The fluid delivery device of claim 1, further comprising a delivery device in fluid communication with the sleeve opening, wherein the delivery device is configured to selectively apply the fluid to be delivered to a desired location.

3. The fluid delivery device of claim 1, wherein one of the first end and the second end is sealed opposite the sleeve opening.

4. The fluid delivery device of claim 1, wherein the outer wall and the inner wall are tubular.

5. The fluid delivery device of claim 1, wherein the outer wall entirely surrounds the inner wall.

6. The fluid delivery device of claim 1, wherein the outer wall and the inner wall comprise at least one plastic.

7. The fluid delivery device of claim 1, wherein the outer wall and the inner wall are comprised of different plastics.

8. The fluid delivery device of claim 1, wherein at least one of the outer wall and the inner wall is constructed from CAB (cellulose acetate butyrate).

9. The fluid delivery device of claim 1, wherein the outer wall is constructed from a plasticized material having a first concentration of a plasticizer and the inner wall is constructed from a plasticized material having a second concentration of the plasticizer that is greater than the first concentration.

10. The fluid delivery device of claim 1, wherein one of the walls comprises a plurality of sub-layers coupled to one another.

11. The fluid delivery device of claim 10, wherein the plurality of sub-layers comprises at least two layers of CAB (cellulose acetate butyrate) and a layer of TPU (thermoplastic polyurethane) situated between the at least two layers of CAB (cellulose acetate butyrate).

12. A method of constructing a fluid delivery device comprising the steps of:
providing a breakable container holding a fluid;
forming a sleeve having an outer wall that at least partially surrounds an inner wall, wherein the outer wall and the inner wall are formed separately and independently from one another without a bond between the inner and outer walls, wherein the outer and inner walls are formed so as not to be separable from each other during use, wherein the sleeve defines a cavity having an opening;
positioning the container within the cavity of the sleeve;
wherein the container is configured to be selectively breakable upon application of a transverse squeezing force to the sleeve so as to disperse the fluid within the cavity and enable the fluid to be dispensed through the opening of the container;
wherein, when the transverse squeezing force is applied to the sleeve, the transverse squeezing force is transferred first from the outer wall to the inner wall through an interface between the outer and inner walls, and then from the inner wall to the breakable container so as to break the container, and wherein the outer and inner walls and the interface between the outer and inner walls cooperate to inhibit penetration of the material of the breakable container through the sleeve after the breakable container has been broken by application of the transverse squeezing force.

13. The method of claim 12, further comprising the step of coupling an applicator to the sleeve, wherein the applicator is configured to deliver the fluid from the container to a location exterior of the container.

14. The method of claim 12, wherein the forming step is carried out by a first extruding step wherein the inner wall is extruded, a cooling step in which the inner wall is cooled, and a second extruding step in which the outer wall is extruded at least partially over the inner wall.

15. A fluid delivery device comprising:
a sleeve having a first end and a second end opposite the first end, the sleeve defining an opening at one of the first and second ends and a cavity between the first end and the second end, and wherein the sleeve is constructed from at least a first wall and a second wall that are arranged independently and separately from one another in which the first wall at least partially surrounds the second wall, wherein the first wall is constructed from a plasticized material having a first concentration of a plasticizer and the second wall is constructed from a plasticized material having a second concentration of the plasticizer that is greater than the first concentration;
a container located within the cavity for holding a fluid to be delivered, and wherein the container is selectively crushable to disperse the fluid to be delivered within the cavity.

16. A fluid delivery device comprising:
a sleeve having a first end and a second end opposite the first end, the sleeve defining an opening at one of the first and second ends and a cavity between the first end and the second end, and wherein the sleeve is constructed from at least a first wall and a second wall that are arranged independently and separately from one another in which the first wall at least partially surrounds the second wall, wherein the second wall comprises a plurality of sub-layers coupled to one another, wherein the plurality of sub-layers comprises at least two layers of CAB (cellulose acetate butyrate) and a layer of TPU (thermoplastic polyurethane) situated between the at least two layers of CAB (cellulose acetate butyrate);

a container located within the cavity for holding a fluid to be delivered, and wherein the container is selectively crushable to disperse the fluid to be delivered within the cavity.

17. The fluid delivery device of claim 1, wherein the sleeve is formed by first forming the inner wall in a first forming operation and subsequently forming the outer wall over the inner wall in a second forming operation separate from the first forming operation.

18. The fluid delivery device of claim 1, wherein the sleeve is formed in a coextrusion process in which the outer wall and the inner wall are formed at the same time and in a manner such that a bond is not formed between the outer wall and the inner wall.

19. The method of claim 12, wherein the outer wall and the inner wall are formed by first forming the inner wall in a first forming operation and subsequently forming the outer wall over the inner wall in a second forming operation separate from the first forming operation.

20. The method of claim 12, wherein the outer wall and the inner wall are formed in a coextrusion process in which the outer wall and the inner wall are formed at the same time and in a manner such that a bond is not formed between the outer wall and the inner wall.

* * * * *

UNITED STATES PATENT AND TRADEMARK OFFICE
CERTIFICATE OF CORRECTION

PATENT NO. : 8,708,196 B2  Page 1 of 1
APPLICATION NO. : 13/328266
DATED : April 29, 2014
INVENTOR(S) : Joseph J. Spitz et al.

It is certified that error appears in the above-identified patent and that said Letters Patent is hereby corrected as shown below:

IN THE CLAIMS

Claim 1, column 7, line 36, delete "farce" and substitute therefor -- force --.

Signed and Sealed this
Fifteenth Day of July, 2014

Michelle K. Lee
*Deputy Director of the United States Patent and Trademark Office*